(12) United States Patent
Kang et al.

(10) Patent No.: US 6,605,469 B1
(45) Date of Patent: Aug. 12, 2003

(54) NUCLEIC ACID MOLECULE ENCODING A CYTOCHROME P-450 HYDROXYLASE IN BRASSINOSTEROID BIOSYNTHESIS IN PLANTS

(75) Inventors: Jeong-Gu Kang, Buk-Gu (KR); Chung-Mo Park, Buk-Gu (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 30 days.

(21) Appl. No.: 09/689,783

(22) Filed: Oct. 13, 2000

(51) Int. Cl.$^7$ .......................... C12N 1/21; C12N 15/80; C12N 15/82; C12N 15/85; C12N 15/29
(52) U.S. Cl. ............... 435/419; 435/252.3; 435/252.33; 435/254.11; 435/325; 536/23.2; 536/23.6
(58) Field of Search ............................. 435/320.1, 419, 435/468, 325, 252.3, 252.33, 254.11; 536/23.6, 23.2; 800/278, 298

(56) References Cited

PUBLICATIONS

Brugliera et al, "Isolation and characterization of a flavonoid 3'-hydroxylase cDNA clone corresponding of Petunia hybrida", 1999, The Plant Journal vol. 19, No. 4, pp. 441–451.*
Jones et al, "Specificity of resistance to pea seed–borne mosaic potyvirus in transgenic pease expressing the viral replicase (NIb) gene", 1998, Journal of General Virology, vol. 79, pp. 3129–3137.*
Czernic et al, "Characterization of hsr201 and hsr515 . . . provoked by phytopathogenic bacteria", 1996, Plant Molecular Biology vol. 31, pp. 255–265.*
GenBank Accession No. X95342, Sep. 1996.*
GenBank Accession No. AF155332 Sep. 1999.*
Albrecht von Armin et al.; "Light Control of Seedling Development"; *Annu. Rev. Plant Physiol.;* Plant Mol. Biol.; vol. 47; pp. 215–243; 1996.
Ricardo Azpiroz et al.; "An Arabidopsis Brassinosteroid–Dependent Mutant is Blocked in Cell Elongation"; *The Plant Cell;* vol. 10; pp. 219–230; Feb. 1998.
Gerard J. Bishop et al.; "The Tomato DWARF Enzyme Catalyses C–6 Oxidation in Brassinosteroid Biosynthesis"; *Proc. Natl. Acad. Sci;* Plant Biology; vol. 96; pp. 1761–1766; Feb. 1999.

Sunghwa Choe et al.; "The DWF4 Gene of Arabidopsis Encodes a Cytochrome P450 That Mediates Multiple 22α–Hydroxylation Steps in Brassinosteroid Biosynthesis"; *The Plant Cell;* vol. 10, pp. 231–243; Feb. 1998.
Steven D. Clouse et al.; BRASSINOSTEROIDS: Essential Regulations of Plant Growth and Development; *Annu. Rev. Plant Physiol.;* Plant Mol. Biol.; vol. 49; pp. 427–451; 1998.
Shozo Fujioka et al.; "The Arabidopsis *Deetiolated2* Mutant is Blocked Early in Brassinosteroid Biosynthesis"; *The Plant Cell;* vol. 9; pp. 1951–1962; Nov. 1997.
Jianming Li et al.; "A Role for Brassinosteroids in Light–Dependent Development of Arabidopsis"; *Science;* vol. 272; pp. 398–401; Apr. 19, 1996.
Yukio Nagano et al.; "Location of Light–Repressible, Small GTP–Binding Protein of the YPT/*rab* Family in the Growing Zone of Etiolated Pea Stems"; *Proc. Natl. Acad. Sci.;* Plant Biology; vol. 92; pp. 6314–6318; Jul. 1995.
Miklós Szekeres et al.; "Brassinosteroids Rescue the Deficiency of CYP90, a Cytochrome P450, Controlling Cell Elongation and De–etiolation in Arabidopsis"; *Cell;* vol. 85; pp. 171–182; Apr. 19, 1996.
David J. Waxman; "P450–Catalyzed Steroid Hydroxylation: Assay and Product Identification by Thin–Layer Chromatography"; *Methods in Enzymology;* vol. 206; pp. 462–476; 1991.

\* cited by examiner

*Primary Examiner*—Phuong T. Bui
*Assistant Examiner*—Cynthia Collins
(74) *Attorney, Agent, or Firm*—Oliff & Berridge, PLC

(57) ABSTRACT

The present invention provides a nucleic acid molecule encoding a dark-inducible cytochrome P450 hydroxylase that catalyzes the brassinosteroid biosynthesis through C-2 hydroxylations in plants. The invention also describes the methods and processes for generating expression cassettes and plasmids and for the use of these expression cassettes and plasmids to synthesize the cytochrome P450 hydroxylase or biologically active fragments of such an enzyme. The invention can be utilized to improve or decrease the stem growth of transgenic plants containing the nucleic acid molecule so that they exhibit improved growth rate and resistance to environmental stress and to identify other proteins involved in the brassinosteroid biosynthesis and in the plant growth regulation.

6 Claims, 7 Drawing Sheets

A
```
  1  MALQVLTLPSWVTLFTTFAILLLFSRRLRRRQYNLEEGRKPKPIGNFNL
 51  IGTLPHQSLRGLTQKYGPIMHLWFGSKRVVVGSTVEMAKAFLKTHDATLA
101  GRPKFSAGKYTTYNYSDITWSQYGPYWRQARRMCLLELFSAERLESYEYI
151  PRQELIIVFRHELFDSRNKTILLKDHLSSLSLRVISRMVLGRKYLEKVENS
201  TISPDLFKDMLDELFLLNGILNIGDFIPWIHFLDFQGYVKIHKVLSEKED
251  GFMEHVLEEHIERRKGVKDYVAKDMVDVLLQLAEDPDLEVKLERHGVKAF
301  TQDLIAGGTESSAVTVEWAISELIRKPEIFKKATEELDRVIGRERWVEEK
351  DIANLPYVYAIAKETMRLHPVAPMLVPREAREDCNINGYDIPKGSLILVN
401  TWTIARDSRVWDNPNEFMPERFLGKDIDVKGHDYELLPFGAGRRMCPGYP
451  LGIKVIQSSLAMLLHGFNWRLSDDVKKEDLNMEEIFGLSTPKKIH   495
```

B
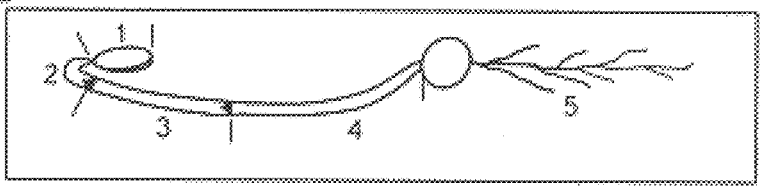

C
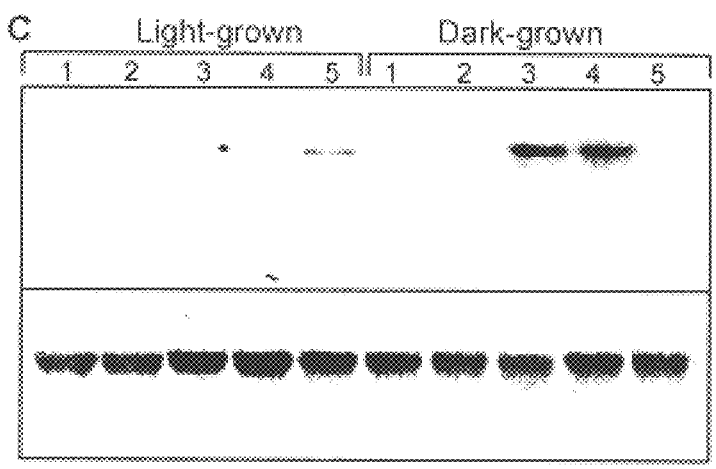

FIG. 1

NUCLEIC ACID MOLECULE ENCODING A CYTOCHROME P-450 HYDROXYLASE IN BRASSINOSTEROID BIOSYNTHESIS IN PLANTS

BACKGROUND OF THE INVENTION

The present invention is to provide a nucleic acid molecule encoding a cytochrome P450 hydroxylase that catalyzes the brassinosteroid biosynthesis in plants, the methods and processes for generating and analyzing biologically active polypeptides encoded by the nucleic acid molecule, and the identification and characterization of other signaling proteins that regulate the brassinosteroid biosynthesis.

Light regulates virtually all aspects of plant growth and developmental processes, among which seedling development is the most sensitive to light condition (Arnim and Deng, 1996; Chory, 2000). Plants therefore possess sophisticated systems for light signal perception and transmission. Light signals are perceived by various photoreceptors, including the red and far-red light absorbing phytochromes (Quail, 1997), the blue/UV-A light absorbing cryptochromes/phototropin (Briggs and Huala, 1999), and the UV-B light absorbing receptor (Senger and Schmidt, 1994). The light signals are subsequently transmitted through various signal transducers and finally regulate genes involved in plant photomorphogenesis. Light does not function independently but is integrated with endogenous growth regulators, such as growth hormones, for temporal and spatial regulation of growth and development (Szekeres et al., 1996; Schumacher and Chory, 2000).

Recent studies on photomorphogenic mutants suggest that brassinosteroids (BR), auxin, and gibberellins (GA) are involved in the photomorphogenic processes, particularly stem morphogenesis and leaf development (Li et al., 1996; Kim et al., 1998; Friedborg et al., 1999; Kamiya et al., 1999). Among them, the most extensively studied is the interaction between light and BR (Szekeres et al., 1996; Clouse and Sasse, 1998; Schumacher and Chory, 2000). BR-deficient mutants exhibit photomorphogenic development in the dark, such as chlorophyll synthesis, apical hook and cotyledon opening, and thick dwarfish hypocotyls (Fujioka et al., 1997). In the light they show dwarfish stems and petioles, dark-green leaves, male sterility, and delayed senescence, primarily due to retarded cell elongation in stems and pollen tubes (Li et al., 1996; Szekeres et al., 1996). These observations indicate that BR hormones possess an essential role in plant growth and developmental processes, including cell elongation and division, etiolation, reproductive development, and vascular differentiation (Clouse and Sasse, 1998).

BR hormones are synthesized through a multi-step biosynthetic pathway by a series of enzymes in plants. The biosynthetic steps have been elucidated using cultured cells and seedlings of *Catharanthus roseus* and by feeding experiments of BR-deficient mutants (Clouse and Sasse, 1998; Fujioka et al., 2000). The enzymes characterized so far include sterol desaturases (DWF7/STE1) (Choe et al., 1999b), oxidases (DWF1/DIM1/LKB) (Choe et al., 1999a; Nomura et al., 1999), reductases (DET2/LK) (Li et al., 1996), and cytochrome P450 hydroxylases (DWF4, CPD/DWF3, D) (Choe et al., 1998; Bishop et al., 1999). An Arabidopsis mutant bri1 and a pea mutant lka are insensitive to BR and have mutations in BR perception (Li and Chory, 1997; Nomura et al., 1999). The BRII gene encodes a leucine-rich repeat (LRR) receptor with the cytoplasmic serine/threonine kinase domain and the external putative BR binding LRR domain (Li and Chory, 1997). The external LRR domain has been recently confirmed to respond to BR (He et al., 2000). Several proteins, such as expansins (Cosgrove, 1997), endo-1,4-β-D-glucanases (Nicol et al., 1998), and xyloglucan endotransglycosylase (Xu et al., 1995), respond to BR signals. Interestingly, the BR-responsive proteins have been implicated to be primarily responsible for the cell wall modification in the cell elongation and related process, which are primary developmental processes regulated by light and BR (Salchert et al., 1998; Azpiroz et al., 1998).

Roles of a variety of signaling mediators have been confirmed or suggested in light signal transduction pathway in plants, including guanosine triphosphatases (GTPases), $Ca^{2+}$/calmodulin, phospholipase C, and protein kinases/phophatases (Roux, 1994). Heterotrimeric GTPases modulate the light signal transduction in plants through interaction with cGMP and/or $Ca^{2+}$ (Bowler et al., 1994; Hooley, 1998). Monomeric small GTPases, another group of GTPases that belong to the Ras superfamily, regulate numerous cellular processes in animals and plants, such as cell growth and differentiation, cell morphogenesis, and vesicle transport (Ma, 1994; Exon, 1998). Accumulating evidences support that they also fulfill a role in the light signal transduction in plants (Romero et al., 1991; Sommer and Song, 1994; Nagano et al., 1995). Of particular interest is the pea Pra2 small GTPase. The expression is dark-inducible and down-regulated by the light (Yoshida et al., 1993). It is thus notable that the 5' nontranslating region of the pra2 gene contains a dark-inducible element, DE1, that confers light down-regulation of a reporter gene (Inaba et al., 2000). The Pra2 is expressed exclusively in the rapidly elongating upper region of the epicotyls in the dark (Nagano et al., 1995). It is interesting that this plant part is the site where total phytochrome content is the richest among different plant parts (Briggs and Siegelman, 1965) and most sensitive to BR treatment in BR-deficient dwarfish mutants (Azpiroz et al., 1998). These observations propose that the Pra2 plays a regulatory role in the integration of light signals with plant growth hormones, most probably BR hormones, for the regulation of etiolated seedling development (Arnim and Deng, 1996).

In this work, we show that the Pra2 specifically interacts with a noble cytochrome P450 enzyme involved in the BR biosynthesis. The P450 is dark-inducible and predominantly expressed in the rapidly elongating region of the epicotyls, like the Pra2. The Pra2 and cytochrome P450 proteins are colocalized to endoplasmic reticulum (ER). Transgenic plants with reduced Pra2 exhibits dwarfish hypocotyls in the dark, which is completely rescued by BR but not by other growth hormones. The cytochrome P450 mediates multiple C-2 hydroxylations in the BR biosynthesis. Surprisingly, transgenic plants overexpressing the cytochrome P450 show elongated stems even in the light, which phenocopies the hypocotyls of dark-grown seedlings. These results indicate that the Pra2 is a light-regulated molecular switch that regulates the hypocotyl elongation in etiolated seedlings through interaction with the cytochrome P450. The Pra2-P450 interaction could be a molecular mechanism underlying the dark developmental process (etiolation) in plants.

SUMMARY OF THE INVENTION

The present invention relates to nucleic acid molecules encoding a cytochrome P450 hydroxylase or biologically active fragments of such a protein that catalyze the conversion from typhasterol to castasterone via C-2 hydroxylations in the brassinosteroid biosynthesis in plants. Such nucleic acid molecules preferentially encode a protein with the amino acid sequence as given in SEQ ID NO: 2 or fragments thereof that possess the enzymatic activity of the above-described cytochrome P450-like hydroxylase.

The present invention also relates to nucleic acid molecules that hybridize under high stringent conditions to a nucleic acid molecule as given in SEQ ID NO: 1. The term "hybridize under high stringent conditions" means that such nucleic acid molecules hybridize through complementary base pairing under conventional hybridization conditions.

The present invention relates to a polypeptide or biologically active fragments of such a polypeptides encoded by said nucleic acid molecules for the enzymatic analysis. The cytochrome P450 hydroxylase encoded by said nucleic acid molecules exhibits a C-2 hydroxylase activity that is specific to the conversions from typhasterol to castasterone and from 6-deoxotyphasterol to 6-deoxocastasterone. Further, the invention describes a polypeptide of a cytochrome P450 hydroxylase or biologically active fragments of such a polypeptide expressed in bacterial cells that exhibits the C-2 hydroxylation. The polypeptide encoded by the above-described nucleic acid molecules shares common structural and functional properties, such as molecular weights, electrophoretic mobility, chromatographic behavior, enzymatic activity, and structural and functional domains for N-terminal membrane anchoring region, the proline-rich region, and for the binding of dioxygen, heme, and steroid.

The invention also relates vectors, expression cassettes, and plasmids used in genetic engineering that contain the nucleic acid molecule as described above according to the invention.

In one aspect the present invention relates to transgenic plant cells and plants containing said nucleic acid molecule, and to experimental processes for the elucidation of other proteins involved in brassinosteroid signaling and of molecular events in the interaction of brassinosteroids and light in plant growth and development. The provision of the nucleic acid molecule according the present invention offers the potential to generate transgenic plants with a reduced or increased brassinosteroid biosynthesis leading to various physiological, morphological, and developmental changes in plants. Technical procedures for the procedures are well known to the person in the art.

With the present invention, it is possible to engineer plant growth and developmental processes, such as stem and leaf growth, in regard to the improvement of growth rate and resistance to environmental damages by introducing a brassinosteroid biosynthetic enzyme into economically important crop plants in an organ-specific manner.

Therefore, the present invention provides: 1. Nucleic acid molecules encoding a cytochrome P450 hydroxylase that catalyzes the conversions from typhasterol to castasterone and from 6-deoxotyphasterol to 6-deoxocastasterone in the brassinosteroid biosynthetic pathway in plants, comprising a nucleotide sequence as given in SEQ ID NO: 1 and 2. An *Escherichia coli* XL1-Blue Ddwf1 (KCTC 0857BP) containing vector pGAD4.2-1 having a nucleic acid molecule with the nucleotide sequence as given in SEQ ID NO: 1 has been deposited at Korean Collection for Type Cultures at #52, Oun-dong, Yusung-ku, Taejon 305-333, Republic of Korea, as International Depositary Authority on Aug. 28, 2000, under the Budapest Treaty.

DESCRIPTION OF THE FIGURES

FIG. 1. DDWF1 protein and expression pattern of ddwf1 gene. (A) Primary structure of the DDWF1 protein (GenBank accession number AF218296). The N-terminal membrane anchor region (italic), the proline-rich region (box), and the binding motifs for dioxygen (thin underlined), steroid (thick underlined), and for heme (bold) are indicated. The cysteine residue to which heme is covalently attached is shaded. The central variable region is shade-boxed. (B) A 6 day-old etiolated pea seedling. Pea seedlings were dissected into bud (1), apical hook (2), stem parts (3 and 4), and root (5) as indicated by numbers, and total RNA was separately extracted from each part. (C) Northern blot analysis. Numbers are equivalent to those in (B). The bottom panel shows 18S ribosomal RNAs probed with a labeled ribosomal DNA.

DETAILED DESCRIPTION OF THE INVENTION

Figure 2:
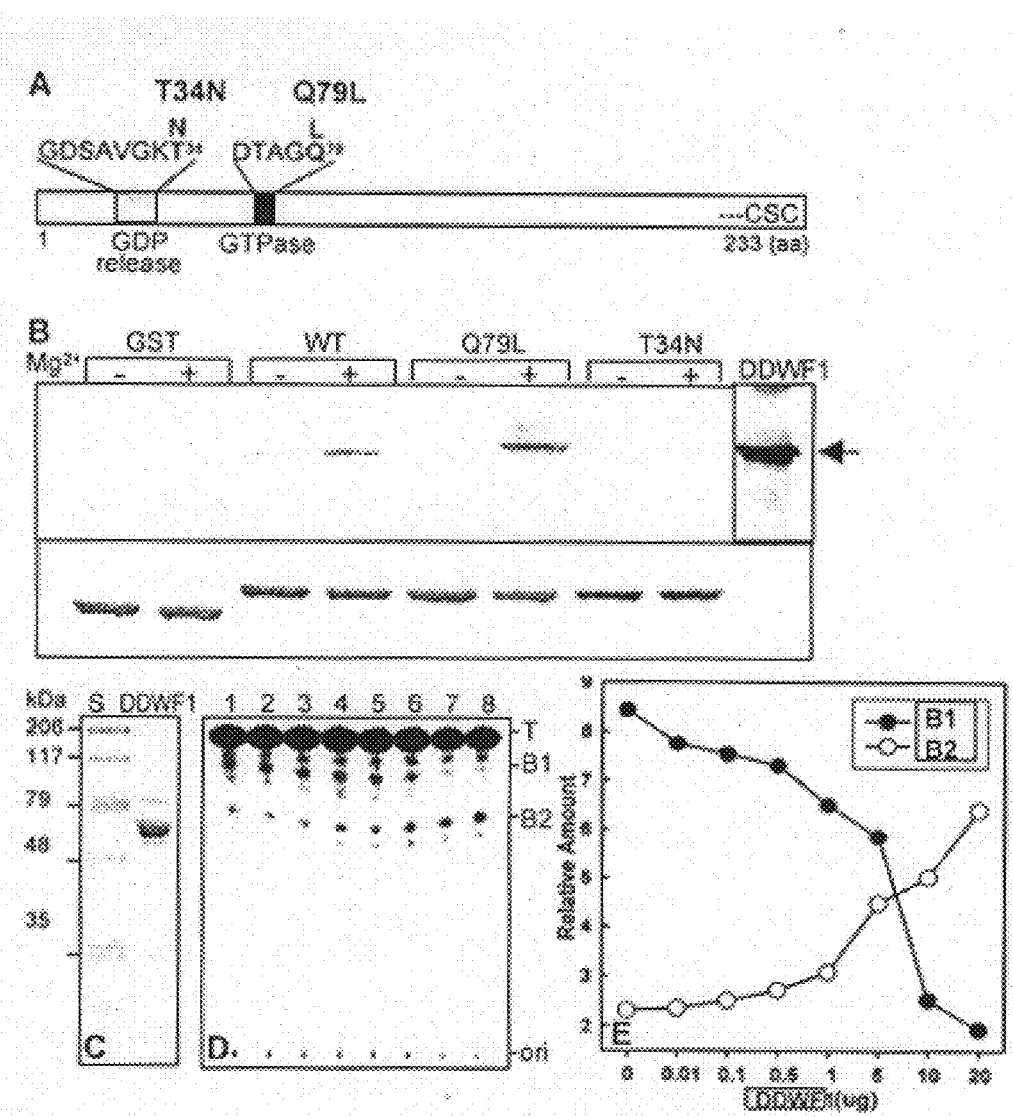
FIG. 2. Pra2-DDWF1 interaction. (A) Pra2 mutants. The $Thr^{34}$ and $Gln^{79}$ were replaced with Asn and Leu to generate a dominant negative form (T34N) and a constitutively active form (Q79L), respectively. (B) In vitro binding of Pra2 with DDWF1. GST was used as a control. Twenty mM magnesium ion was either included (+) or excluded (−). Same amounts of Pra2 and GST proteins were used for each assay (bottom panel). (C) Recombinant DDWF1 protein expressed in *E. coli* cells. (D and E) DDWF1 activity. All reaction mixtures contained identical components except for the DDWF1. Various amounts of DDWF1 were included as indicated in (E). B1 and B2 were predicted to be 6-dehydrotestosterone and 2α-hydroxytestosterone, respectively (Waxman, 1991).

Brassinosteroids has been recently confirmed as essential plant growth regulators, and its biosynthetic pathway and the biosynthetic enzymes have been characterized as a result of extensive physiological and molecular biological studies since the initial isolation of the brassinolide, the most oxidized and active form among brassinosteroids, although their physiological functions and the underlying molecular mechanisms were not fully understood. Brassinosteroids do not work independently but cooperate with other growth regulators and environmental factors, such as light and stress, for the spatial and temporal regulation of plant growth and development. It is therefore important to further elucidate the roles and the working mechanisms of the brassinosteroids and the molecular clues about how they interact with environmental factors.

Thus the present invention provides nucleic acid molecules encoding a cytochrome P450 hydroxylase or biologically active fragments of such a protein that catalyze the conversions from typhasterol to castasterone and from 6-deoxotyphasterol to 6-deoxocastasterone via C-2 hydroxylations in the brassinosteroid biosynthesis in plants. The nucleic acid molecules preferentially encode a protein with the amino acid sequence as given in SEQ ID NO: 2 or fragments thereof that possess the enzymatic activity of the above-mentioned cytochrome P450 hydroxylase. Such a nucleic acid molecule as given in SEQ ID NO: 1 is more preferred. Furthermore, the invention relates to the plasmids and expression cassettes comprising nucleic acid molecules containing the nucleotide sequences as given in SEQ ID NO: 1 for functional expression in prokaryotic and eukaryotic cells. The nucleic acid molecule can be isolated as a full-size cDNA clone by various conventional methods, such as reverse transcriptase-mediated PCR (RT-PCR) using the mRNA or by the screening of a cDNA library using a partial-size cDNA clone as probe, well known techniques to the art. For the RT-PCR method, the poly(A)$^+$ mRNA can be first converted into a primary cDNA using the reverse transcriptase and the oligo(dT)$^{16-18}$ as the primer. An uninterrupted double stranded cDNA can then be synthesized by PCR using a pair of specific primers (SEQ ID NO: 3 and SEQ ID NO: 4).

The present invention also relates to nucleic acid molecules that hybridize under high stringent conditions to a nucleic acid molecule as given in SEQ ID NO: 1. The term "hybridize under high stringent conditions" means that such nucleic acid molecules hybridize through complementary base pairing under conventional hybridization conditions, as described in Sambrook et al., (Molecular Cloning: A Laboratory Manual, 2$^{nd}$ Ed., Cold Spring Harbor Laboratory, Cold Spring Harbor, N.Y., 1989). Nucleic acid molecules hybridizing with the above nucleic acid molecule include in general those from any plants, preferentially from plants of interests in agriculture, forestry, and horticulture, such as rice, barley, wheat, oilseed rape, potato, tomato, cabbage, lettuce, spinach, melon, watermelon, green onion, radish, cauliflower, sugar cane, cucumber, and sugar beet. Woody plants are also preferred sources. To isolate a nucleic acid molecule that hybridize to the nucleic acid molecule as given in SEQ ID NO: 1, a cDNA or a genomic DNA library is screened using the the-above described nucleic acid molecule as probe, a molecular biological technique well known to the art.

According to the present invention, the term "degenerate" means that the nucleotide sequences of nucleic acid molecules are differ from the above-described nucleic acid molecules in one or more base positions and highly homologous to said nucleic acid molecules. "Homologous" indicates an amino acid sequence identity of at least 70%, particularly 80% or higher. The term also includes derivatives of the nucleic acid molecules as described above by insertions, deletions, base substitutions, and recombinations. The "homologous" also describes that the nucleic acid molecules or the polypeptides encoded by said nucleic acid molecules are structurally and functionally equivalent.

Furthermore, the present invention relates to a polypeptide or biologically active fragments of such a polypeptide encoded by said nucleic acid molecule for the use in the enzymatic analysis and biochemical assays. One efficient way to get such a polypeptide is to use the recombinant expression systems. To do that, the nucleic acid molecule is first inserted into an expression vector containing regulatory elements required for efficient expression of the polypeptide encoded by said nucleic acid molecule, such as promoters, terminators, and polyadenylaton signals. The expression cassettes are then transfected into appropriate host cells. The host cells can be prokaryotic or eukaryotic. For efficient isolation of the expressed polypeptide from the host cell culture, affinity tags are attached to the polypeptide. The tags can be easily removed from the fusion proteins after isolation by enzymatic or biochemical methods, a recently well-established skill to the art.

The enzymatic activity of the cytochrome P450 hydroxylase encoded by said nucleic acid molecule can be assayed using a general hydroxylation substrate, such as the testosterone or its derivatives which have similar chemical structures to those of the brassinosteroids, or brassinosteroids. The reaction mixture is then analyzed on thin layer chromatography (TLC) or on HPLC. The cytochrome P450 in the present invention has a C-2 hydroxylase activity in the conversions from typhasterol to castasterone in the early C-6 oxidation pathway and from 6-deoxotyphasterol to 6-deoxocastasterone in the late C-6 oxidation pathway in the brassinosteroid biosynthesis. The polypeptide encoded by the above-described nucleic acid molecule share common structural and functional properties with cytochrome P450 enzymes, such as molecular weights, electrophoretic mobility, chromatographic behavior, enzymatic activity, and structural and functional domains for N-terminal membrane anchoring region, the proline-rich region, and for the bindings of dioxygen, heme, and steroid, but exhibits a distinct substrate specificity.

The present invention also relates vectors, expression cassettes, and plasmids used in genetic engineering that contain the nucleic acid molecule as described above according to the invention.

In one aspect the cytochrome P450 hydroxylase encoded by said nucleic acid molecule in the present invention specifically interacts with a small molecular weight GTP-binding protein, the Pra2 isolated from *Pisum sativum*, that belongs to the Ras superfamily, in a GTP-dependent manner like other characterized GTPase-effector interactions. The above-mentioned polypeptide is localized to endoplasmic reticulum (ER). On the contrary the Pra2 localization to ER is GTP-dependent. Only the GTP-bound active form associates with ER. The colocalization of the two proteins to ER can be examined by attaching fluorescent proteins to the two proteins, resulting in fusion proteins, by expressing the fusion constructs in transgenic plants, and by examining under fluorescent microscope.

The present invention can be utilized to generate transgenic plant cells and plants containing said nucleic acid molecule and to the processes and methods for the elucidation of other proteins involved in brassinosteroid signaling and of molecular events in the interaction of brassinosteroids with light. The provision of the nucleic acid molecules according to the present invention offers the potential to generate transgenic plants with a reduced or increased brassinosteroid biosynthesis leading to various physiological, morphological, and developmental changes. Technical procedures for the generation of transgenic plant cells and plants are well known to the art.

With recent technical advances in plant tissue culture and manipulation of genetic materials, it is at present a routine procedure to introduce a new desired gene into economically important plants to improve plant productivity and quality. The nucleic acid molecule in the present invention can be a potential target gene for such purpose. For example it can be utilized to engineer plant growth and developmental processes, such as stem and leaf growth, in regard to the improvement of growth rate and resistance to environmental damages. The desired plant plants for the embodiment of the present invention include any of valuable plants in agriculture, forestry, and horticulture, such as rice, corn, sugar cane, turf grass, melon, watermelon, cucumber, pepper, and popular tree. Plants in horticulture whose quality can be improved by engineering stem growth are also good target plants for the embodiment of the present invention.

EXAMPLES

Plant Materials and Growth Conditions

Seeds of Nicotiana tabacum (Petit Havana SR1) were germinated and grown in sterile condition at 25° C. with a 16-hour photoperiod. The Arabidopsis thaliana ecotype Columbia (Col-0) was germinated and grown on 0.5× Murashige and Skoog medium containing 1% agar and Suc. All Arabidopsis cultures were maintained in a controlled environment culture room at 22° C. with the humidity of 70% and the photoperiod of 12 hours. Feeding experiments were also performed in the same culture conditions.

Yeast Two-Hybrid Screening

Yeast two-hybrid screening was carried out using the MATCHMAKER Two-Hybrid System as described by the manufacturer (Clontech, Palo Alto, Calif.). The full-size pra2 gene was cloned into the bait plasmid pGBT9. The pea cDNA library was constructed from 6 day-old dark-grown seedlings and cloned into the phagemid vector pAD-GAL4-2.1. The bait plasmid construct was first transformed into a yeast strain HF7c by electroporation, which was subsequently transformed with the cDNA library phagemid construct. Final positive transformants (his3$^+$ and LacZ$^+$) were selected in the presence of 20 mM aminotriazole to eliminate false positives. The positive clones were isolated by back transformation into E. coli strain XL1-Blue.

Expression and Purification of Recombinant Proteins

The pra2 gene sequences were cloned into the pGEX-4T-2 vector (Amersham-Pharmacia, Buckinghamshire, UK) in a way that the 5' end was in frame fused with the vector sequence encoding the glutathione-S-transferase. All vector constructs were confirmed by DNA sequencing using the ABI PRISM 310 Genetic Analyzer (Perkin Elmer, Foster City, USA). The QuickChange Kit (Promega, Madison, Wis.) was used for in vitro mutagenesis of the pra2 gene as described by the manufacturer. The expression constructs were transformed into E. coli strain BL21 and selected with 100 μg/ml ampicillin. The E. coli cells were grown in 5 ml of LB medium at 37° C. overnight, and 3 ml of the culture was transferred into 250 ml of RB medium (0.5% yeast extract, 1% tryptone, 0.5% NaCl, 0.2% glucose, pH 7.5) and shaked at 30° C. until the OD$_{600}$ reached 0.55 to 0.6. The culture was then adjusted to 30° C. for 30 min, and the expression was induced by adding IPTG (isopropyl-β-D-thiogalactopyranoside) to a final concentration of 1 mM and by shaking for additional 4 hours. The Pra2-GST fusion proteins were purified by glutathione sepharose 4B-based affinity chromatography (Promega).

The DDWF1 protein was expressed via the Intein-based expression vector pTYB2 (NEB, Beverly, Mass., USA) as a soluble form in E. coli cells. The ddwf1 gene was inserted into the pTYB2 vector in a way that the C-terminus of the coding sequence was in frame fused to the vector sequence encoding the Intein polypeptide. The expression construct was transformed into E. coli strain ER2566. The cells were grown in he same way as with the Pra2 proteins. The DDWF1-Intein fusion protein was purified by chitin affinity chromatography as suggested by the supplier and in-column cleaved by 1 mM DTT at 4° C. overnight to release the DDWF1 polypeptide. In this expression scheme, two additional amino acid residues (Pro and Gly) were attached to the C-terminus of the DDWF1 as a result of cloning procedure.

In Vitro Binding Assays with Recombinant Proteins

The ddwf1 gene was cloned into the pGEM3Z(+) and in vitro translated using the TNT Quick Coupled Transcription/Translation System (Promega). About 1 μg of vector DNA template and 20 μCi of [$^{35}$S]-methionine (Amersham, Cat. No. AG1094) were used in a 50 μl reaction volume. The reaction mixture was incubated at 30° C. for 90 min and quick-frozen at −70° C. until use. Two μg of the Pra2-GST fusion protein was first bound to glutathione sepharose 4B resin either in the presence or absence of 0.5 mM GTP in an Eppendorf tube. Five μl of the in vitro translated mixture was added, and the mixture was incubated at 30° C. for 30 min. The resin was then thoroughly washed 3 times with PBS buffer, and the bound DDWF1 was eluted and analyzed by SDS-PAGE and autoradiography.

Subcellular Colocalization Analysis

The GFP and RFP (Clontech) were in frame fused to the N-terminus of the Pra2 and to the C-terminus of the DDWF1, respectively. The fusion constructs were subcloned into the pBI221 binary vector (Clontech). The vector constructs were transiently expressed in onion epidermal cells after transfection by particle bombardment. After 24 hours of incubation, subcellular distributions of the fusion proteins were examined by fluorescence microscope. As a control for ER association, the ER-GFP that contained an ER signal peptide at the N-terminus was used. The GFP and RFP were also included as controls for nonspecific distribution throughout the cytoplasm and nucleus.

Plant Transformation

The ddwf1 gene was cloned into the pBI121 vector. Plant expression constructs were transformed into tobacco plants via the Agrobacterium tumefaciens infection of leaf disks essentially as previously described (Horsch et al., 1985). Kanamycin and cefotaxime were used for selection of transformants at 200 mg/ml and 500 mg/ml, respectively. The Agrobacterium-mediated transformation of Arabidopsis plants was performed by a simplified floral dip method (Clough and Bent, 1998).

RNA Extraction and Northern Hybridization

Total RNA samples were isolated from appropriate plant materials using the Rnasey Plant Total RNA Isolation Kit (Qiagen, Valencia, Calif.) according to the procedure provided by the manufacturer. RNA samples were denatured in MOPS buffer (20 mM MOPS, 8 mM sodium acetate, 1 mM EDTA) supplemented with 50% (v/v) formamide and 2.2 M formaldehyde at 65° C. for 10 min and fractionated on a 1% agarose gel prepared in the same buffer. The probes were prepared by random priming in the presence of $\alpha$-[$P^{32}$] dATP. Transfer onto Hybond-N membrane and subsequent processing were carried out as previously described (Sambrook et al., 1989).

Complementation with BR Hormones and Other Growth Regulators

Plant growth regulators tested were BR, GA, auxin, cytokinine, abscisic acid, and salicylic acid. The BR hormones included the most oxidized brassinolide (BL, $10^{-8}$ M) and various intermediates, such as campestanol (CN, $10^{-6}$ M), 6-oxocampestanol (6-oxoCN, $10^{-6}$ M), 6-deoxocathasterone (6-deoxoCT, $10^{-6}$ M), cathasterone (CT, $10^{-6}$ M), 6-deoxoteasterone (6-deoxoTE, $10^{-6}$ M), teasterone (TE, $10^{-6}$ M), 6-deoxotyphasterol (6-deoxoTY, $10^{-7}$ M), typhasterol (TY, $10^{-7}$ M), 6-deoxocastasterone (6-deoxoCS, $10^{-8}$ M), 6$\alpha$-hydroxycastasterone (6-OHCS, $10^{-8}$ M), and castasterone (CS, $10^{-8}$ M). Each BR intermediates were used at the concentrations as indicated in parentheses. The concentrations used were determined by a series of titrations so that the wild type plant did not show any inhibitory effects at given concentrations. Plants were germinated and grown in the presence of each BR intermediate for 4–7 days either in the light or in complete darkness. Hypocotyl lengths of 30–50 plants in each treatment were measured and averaged.

Assays of DDWF1 Activity

Forty $\mu$l of the [4-$^{14}$C]testosterone (Amersham-Pharmacia, Cat. No. CFA129, 193 $\mu$Ci/mg) was aliquoted, and the solvent was evaporated under gentle stream of $N_2$ gas. Yeast microsomal fractions were prepared as described (Pompon et al., 1996). Thirty $\mu$g of microsomal fraction, 5 $\mu$g of Pra2 protein, and various amounts of the recombinant DDWF1 were used for each reaction, each with 175 $\mu$l of the reaction buffer (1M HEPES, pH 7.4, 0.1 mM EDTA, 0.5 mM GTP, 10 mM $MgCl_2$). The mixture was transferred to the tube containing the lyophilized testosterone and incubated for 10 min at 37° C. Twenty-five $\mu$l of NADPH solution, prepared in the same reaction buffer, was then added to the mixture to a final concentration of 1 mM. The total mixture was further incubated for 30 min at 37° C. and terminated by adding 1 ml of ethyl acetate and vortexing for 30 sec. After centrifugation for 4 min at 15000×g, the upper layer was recovered and evaporated in chemical hood overnight. The dry pellet was dissolved in 20 $\mu$l of ethyl acetate, spotted on TLC on Silicagel 60 $F_{254}$ (20×20 cm, Merck, Darmstadt, Germany), and developed in dichloromethane/acetone (4:1 by volume) and then in chloroform/ethyl acetate/ethanol (4:1:0.7 by volume) as described (Waxman, 1991).

For HPLC analysis, BR intermediates were incubated with the DDWF1 as with testosterone, and the mixture was analyzed on the Waters 626 LC System and Photodiode Array Detector (Waters, Milford, Mass.). The reverse-phase Supelcosil LC-18 (250×4.6 mm, Supelco, Pa., USA) was used at a flow rate of 2 ml/min. The solvents used were 45% acetonitrile for the first 20 min, a gradient of 45% to 100% for the next 20 min, and pure acetonitrile for the last 10 min.

Result

Pra2 Interacts with a Dark-Inducible Cytochrome P450

Predominant distributions of endogenous BR and total phytochromes in the rapidly elongating upper region of the epicotyls, where the Pra2 is also most highly expressed, suggest that the Pra2 may have a regulatory role in the interaction between phytochrome-mediated light signals and BR hormones. A yeast two-hybrid screen was carried out using the full-size pra2 gene as bait and a pea cDNA library to identify the functional target protein(s) that specifically interact with the Pra2. Seventeen positive clones that expressed both reporter genes (his3$^+$ and lacZ$^+$) were isolated from the screening of 6.3×10$^6$ clones. Sequence analyses showed that four of them had cDNA inserts with an identical sequence, ranging from 1.2 to 1.65 kbp in length. The largest cDNA clone (clone 1023) was chosen for further sequence analysis. The cDNA insert contained an uninterrupted open reading frame (ORF) that encoded a polypeptide of 495 amino acids with a calculated molecular mass of 57.2 kDa. Database searches revealed that the polypeptide is a noble cytochrome P450. It contains all structural and functional motifs conserved among different cytochrome P450 proteins (Szekeres et al., 1996), including the N-terminal membrane anchor sequence, the proline-rich region, and the binding motifs for dioxygen, steroid, and heme (FIG. 1A). One structural uniqueness is that the central region (amino acids 160–290) exhibits a diverse sequence from other known cytochrome P450 proteins.

The Cytochrome P450 is Predominantly Expressed in the Rapidly Elongating Region of Epicotyls in the Dark Northern blot analysis detected a predominant 1.8-kb message, which was in agreement with the predicted size of the ORF (FIG. 1C). The expression pattern is unique among known cytochrome P450 genes (Mizutani et al., 1998) in that it is mainly expressed in the rapidly elongating upper region of the pea epicotyls. The expression level is comparatively very low in other plant parts, such as apical buds and hooks and roots (FIGS. 1B and 1C). It is also expressed to some level in the roots of light-grown seedlings, which would be related with the light-stimulated root hair growth (Bibikova et al, 1999). In addition, the expression is dark-induced and drastically decreases upon light illumination. Therefore, we named the cytochrome P450 as DDWF1 (Dark-induced DWF-like protein 1). The dark-induced and organ-specific expression pattern of the ddwf1 gene strikingly coincides with that of the pra2 gene (Nagano et al., 1995), signifying a role for the Pra2-DDWF1 interaction in the regulation of etiolated seedling growth.

Pra2-DDWF1 Interaction is GTP-Dependent

The interaction between the Pra2 and DDWF1 was further investigated by in vitro pull-down assays. A dominant negative form (T34N) and a constitutively active form (Q79L) of the Pra2 protein were generated by in vitro mutagenesis (FIG. 2A) and expressed in *E. coli* cells as glutathione S-transferase (GST) fusions. The T34N and Q79L Pra2 proteins are presumed to be in GDP-bound and GTP-bound conformations in vivo, respectively (Higashijima et al., 1987). The ddwf1 gene was in vitro translated in the presence of $S^{35}$-Met, resulting in a polypeptide with a molecular mass of 57 kDa which is close to the predicted size of the DDWF1. The DDWF1 polypeptide bound strongly with the Q79L Pra2 and weakly with the wild type Pra2 (FIG. 2B). However, it did not bind with the T34N Pra2. In addition, the Pra2-DDWF1 interaction is magnesium ion-dependent as has been observed with other small GTPase-effector interactions (Higashijima et al., 1987). Even the Q79L Pra2 bound with the DDWF1 only in the presence of 20 mM $MgCl_2$. The DDWF1 seems to be specific to the Pra2, since it did not interact with the pea Pra3 small GTPase, which has about 65% sequence identity over the whole sequence to the Pra2 and whose expression is also down-regulated by light (Nagano et al., 1995). No interaction was detected from in vitro pull-down assays between the DDWF1 and the Pra3 small GTPases (data not shown).

We then examined the DDWF1 activity in vitro. The DDWF1 was expressed as a soluble form in *E. coli* cells by removing most of the sequence encoding the N-terminal membrane anchor region (18 amino acids, FIG. 1A and FIG. 2C). Testosterone, which has a similar chemical structure to those of BR hormones, was chosen as a substrate. Testosterone itself was not the substrate for the DDWF1, but an intermediate with a mobility of 0.94 relative to testosterone was converted to another intermediate with a relative mobility of 0.78 (FIG. 2D). The conversion rate was proportional to the amounts of the DDWF1 used, indicating that the conversion is specific to the DDWF1 (FIG. 2E). Comparison of the relative mobilities to the well-established mobility profiles of the testosterone derivatives (Waxman, 1991) suggests that the conversion would be from an intermediate (6-dehydrotestosterone?) to 2α-hydroxytestosterone (B1 and B2 in FIG. 2D, respectively) as a result of the C-2 hydroxylation. When the Pra2 proteins were included, the conversion efficiency was slightly higher with the wild type and Q79L than with the T34N. These results support that the Pra2 regulates the DDWF1 activity in a GTP-dependent manner. Although the difference of conversion rates between Q79L and T34N was not as prominent as that in the GTP-dependent Pra2-DDWF1 interaction, this would be explained by the fact that a N-terminal truncated DDWF1, rather than a full-size one that is expected to associate with ER, was used. In addition, the Pra2-DDWF1 interaction seems to require additional cofactors that were absent in our in vitro enzymatic assay conditions.

Pra2 and DDWF1 are Colocalized to ER

Figure 3:
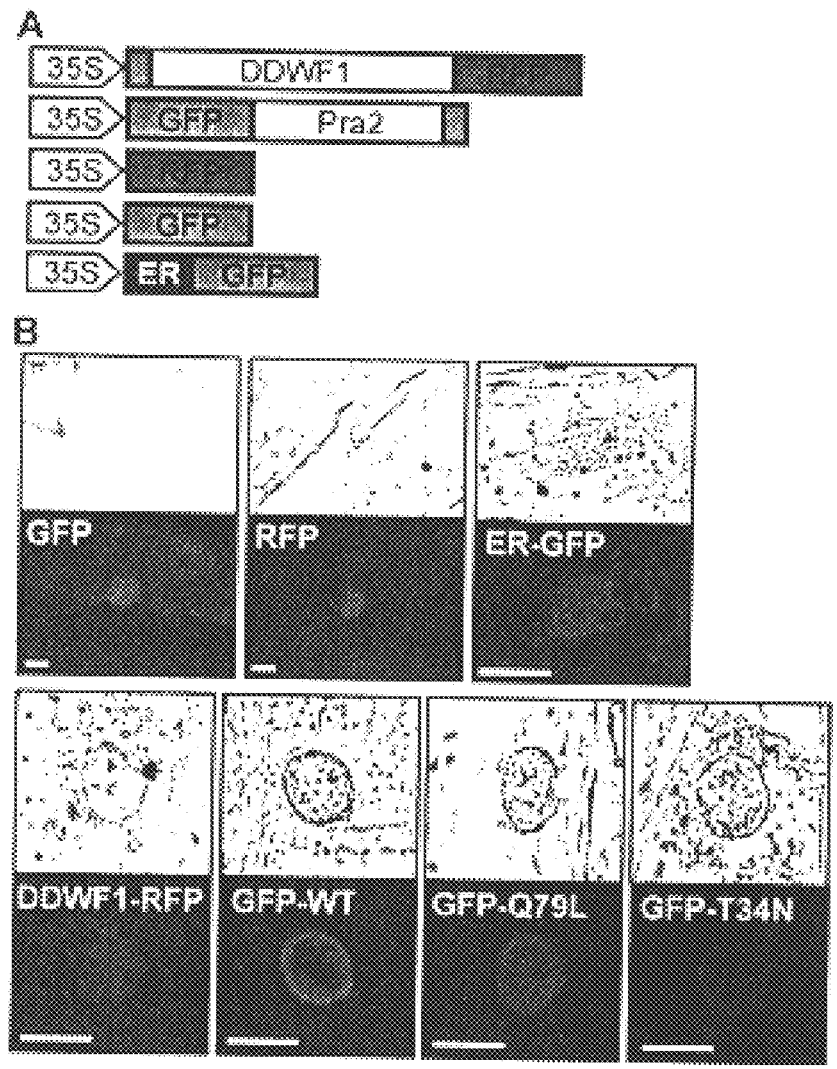
FIG. 3. Colocalization of Pra2 and DDWF1 to ER. (A) Fusion constructs. An ER-specific signal peptide was attached to the GFP and used as a control for ER localization (ER-GFP). GFP and RFP were also included as controls. Blue boxes indicate the membrane anchor motifs. (B) Colocalization of Pra2 and DDWF1. Fusion constructs were transiently expressed in onion epidermal cells and examined under fluorescent microscope. Bars; 10 μm.

Small GTPases have diverse subcellular locations. Furthermore, a given small GTPase changes the subcellular distributions, depending on external and internal signals (Scita et al., 2000). If the Pra2 and DDWF1 are functional partners, they are expected to share the same subcellular location. Two different fluorescent proteins were fused to the Pra2 and DDWF1 proteins, and subcellular localizations of the fusion proteins were examined in transient transfection assays using onion epidermal cells. A green fluorescent protein (GFP) was fused to the N-terminus of the Pra2, and a red fluorescent protein (RFP) to the C-terminus of the DDWF1, resulting in the GFP-Pra2 and DDWF1-RFP fusions, respectively (FIG. 3A). The DDWF1-RFP fusion protein accumulated to ER, predominantly to ER membrane tightly stacked around the nucleus as expected (FIG. 3B). The subcellular distributions of the GFP-Pra2 fusion proteins were GTP-dependent. The wild type Pra2 fusion exhibited an essentially identical localization pattern to that of the DDWF1, mostly bound to ER. The Q79L Pra2 fusion more predominantly accumulated to ER membrane around the nucleus. However the T34N Pra2 fusion did not associated with ER or other membrane structures but was nonspecifically dispersed in the cytoplasm. This colocalization of the Pra2 and DDWF1 to ER membrane further supports-that the Pra2 and DDWF1 proteins are functionally interrelated.

Pra2 Regulates BR Biosynthesis Through Interaction with the DDWF1

Figure 4:
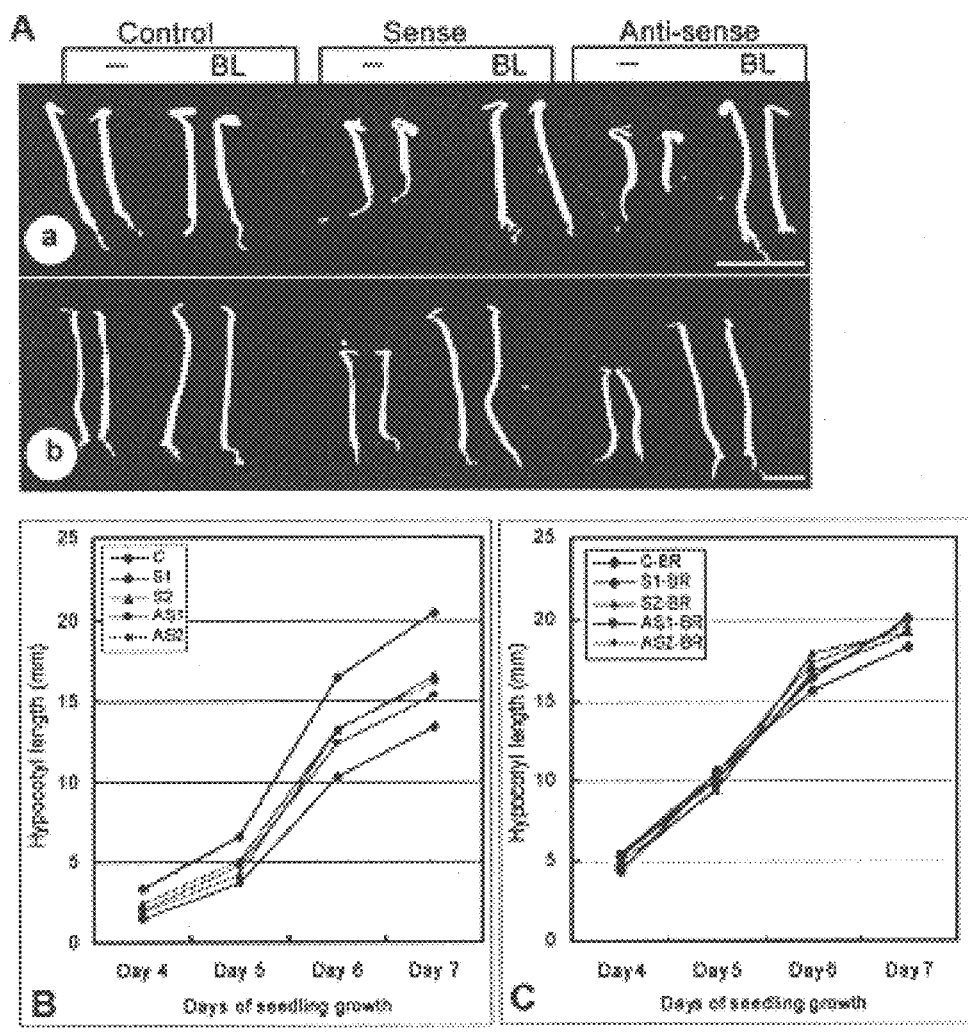
FIG. 4. Pra2 transgenic plants. (A) Dark-grown seedlings of transgenic tobacco plants. Seedling were grown in the dark for 4 days (a) or for 7 days (b) either in the absence (−) or presence (BL) of $10^{-8}$ M brassinolide. Two representative seedlings of each group were shown. (B and C) Growth kinetics of seedlings either in the absence (B) or in the presence (C) of BL. Two homozygotic lines of sense (S1 and S2) and anti-sense (AS1 and AS2) transgenic plants were examined in parallel to a control plant (C). Hypocotyl lengths of 30–50 seedlings of each line were averaged. Bars in (A); 5 mm.

To explore the molecular basis for the Pra2-DDWF1 interaction in plant photomorphogenesis, the pra2 gene was introduced into transgenic tobacco plants. Transgenic plants overexpressing the anti-sense pra2 gene were essentially indistinguishable from control plants when they were grown in the light. However, remarkable phenotypic changes were observed when grown in the dark (FIG. 4A). They exhibited dwarfish thick hypocotyls, a well-characterized trait of BR-deficient plants (Li et al., 1996; Clouse and Sasse, 1998). Histological analysis demonstrated that the dwarfish hypocotyls were not due to decreased cell number but due to reduced cell elongation (data not shown). However, the pra2 transgenic plants were different from known BR-deficient plants in that none of other photomorphogenic traits were observed during the growth period of up to 7 days in the dark. These results are not unexpected since both the pra2 and ddwf1 genes are highly expressed in the rapidly elongating region of the epicotyls but not in apical buds and hooks of etiolated pea seedlings (FIG. 1). Sense transgenic plants also showed similar light responses (FIG. 4A). This could be explained by a cosuppression. Hypocotyl lengths of sense transgenic plants were more variable than those of anti-sense transgenic plants (Matzke and Matzke, 1995). The transcript level of the pra2 sense transgene was very low compared to that of the anti-sense transgene in the transgenic plants (data not shown).

The Pra2 specifically interacts with the DDWF1, an enzyme with high homology to those involved in BR and GA biosynthesis, it was anticipated that the dark-induced dwarfish hypocotyls of the anti-sense pra2 transgenic plants might be due to reduced BR and/or GA biosynthesis. To examine this hypothesis, the transgenic plants were grown in the presence of various phytohormones at physiological concentrations, including BL, GA, auxin, cytokinine, abscisic acid, and salicylic acid. Among the phytohormones tested, only the BL ($10^{-8}$ M) completely rescued the dark-specific dwarfish hypocotyls (FIG. 4A). Other growth hormones did not exhibit any stimulatory effects, although GA showed some effect (about 20–30% of that by BL). No BL effects were observed when transgenic plants were grown in the light as expected. These observations indicate that the anti-sense suppression decreases the level of the Pra2 homologue in the transgenic plants, which subsequently represses the hypocotyl elongation in the dark by down-regulating BR biosynthesis.

There was a possibility that the dwarfish phenotype of the pra2 transgenic plants was simply due to retarded seed germination. To examine this possibility, the kinetics of the seedling growth was analyzed in the absence (FIG. 4B) or presence (FIG. 4C) of BL. The difference of hypocotyl lengths increased as seedlings grew in the absence of BL (FIG. 4B), indicating that the dwarfish phenotype is not simply due to retarded seed germination. The growth kinetics of the transgenic and control plants became similar when they were grown in the presence of BL (FIG. 4C).

DDWF1 Mediates C-2 Hydroxylation Steps in BR Biosynthesis

Figure 5:
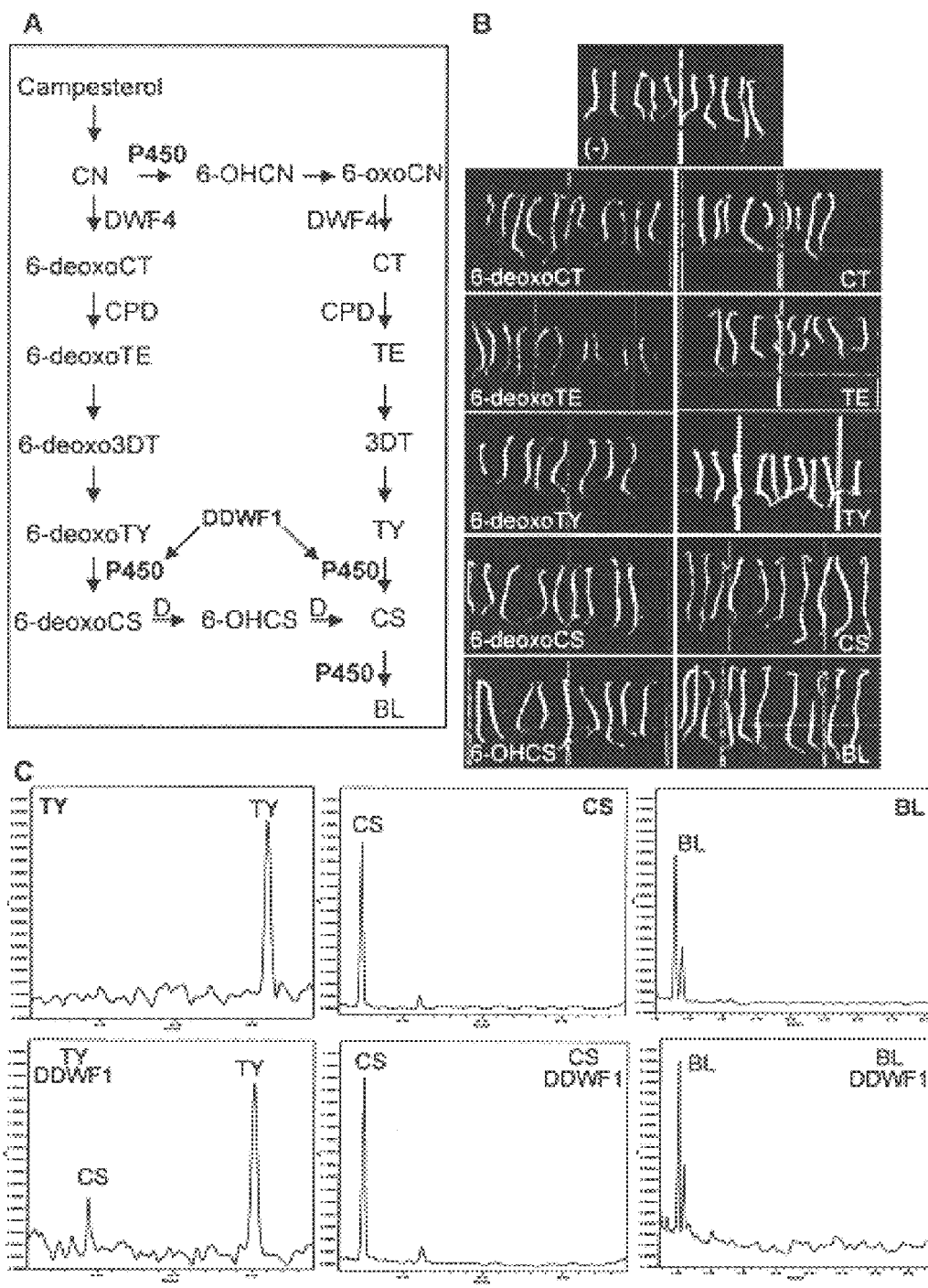
FIG. 5. Feeding experiments with various BR intermediates. (A) The BR biosynthetic pathway. The CPD, DWF4, and D whose activities and substrate specificities have been confirmed are indicated. At least three more cytochrome P450 enzymes are proposed as indicated by 'P450's. (B) and (C) BR feeding experiment. The anti-sense pra2 transgenic plants were grown for 5 days in the presence of BR intermediates in complete darkness (B), and hypocotyls lengths of 30–50 seedlings were measured and averaged (C). (C) Substrate specificity of DDWF1. BR intermediates were treated with DDWF1 and analyzed on HPLC. Results with TY, CS, and BL are shown.

Three cytochrome P450 enzymes have been identified in the BR biosynthetic pathway so far, including the DWF4, CPD (CBB3/DWF3), and D in the conversions from 6-oxocampestanol (6-oxoCN) to cathasterone (CT), from CT to teasterone (TE), and from 6-deoxocastasterone (6-deoxoCS) to CS via 6-hydroxycastasterone (6-OHCS), respectively (Szekeres et al., 1996; Choe et al., 1998; Asami and Yoshida, 1999; Bishop et al., 1999). The DWF4 and CPD also catalyze the corresponding steps in the late C-6 oxidation pathway (FIG. 5A). At least three more P450 enzymes have been implicated in the BR biosynthetic pathway (Asami and Yoshida, 1999; Sakurai and Fujioka, 1997), including the conversion steps from campestanol (CN) to 6-OHCN, from TY to CS, from CS to BL, and from 6-deoxoTY to 6-deoxoCS (FIG. 5A).

To elucidate the biosynthetic step(s) catalyzed by the DDWF1 and interrupted in the pra2 transgenic plants, the pra2 transgenic plants were grown in the presence of various BR intermediates. The BR intermediates tested included CN, 6-deoxoCT, 6-deoxoTE, 6-deoxoTY, 6-deoxoCS, 6-oxoCN, CT, TE, 6-OHCS, TY, CS, and BL. Among these, the CS and BL completely rescued the dwarfish hypocotyls (FIG. 5B). The 6-OHCS and 6-deoxoCS also showed some stimulatory effects, about 50% and 60% of the BL effect, respectively (FIG. 5C). These results indicate that the DDWF1 catalyzes the steps from TY to CS and from 6-deoxoTY to 6-deoxoCS.

To confirm the substrate specificity of the DDWF1, the TY, CS, and BL were treated with the recombinant DDWF1, and the reaction mixtures were analyzed on HPLC (Noguchi et al., 1999). Only the TY was converted to CS (FIG. 5C). However, the CS was not the substrate for the DDWF1. These results, together with the BR feeding results, indicate that the DDWF1 catalyzes C-2 hydroxylations, in agreement with the results of BR feeding data (FIG. 5B). It is also evident that a different P450 mediates the CS to BL conversion. In addition, our data suggest that the early C-6 oxidation pathway seems to be dominant in the dark-grown tobacco plant as has been observed in Arabidopsis, in which the early C-6 oxidation pathway is dominant in the dark and the late C-6 oxidation pathway in the light (Fujioka et al., 1997).

DDWF1 is Functional Exclusively in Hypocotyl Elongation

Figure 6:
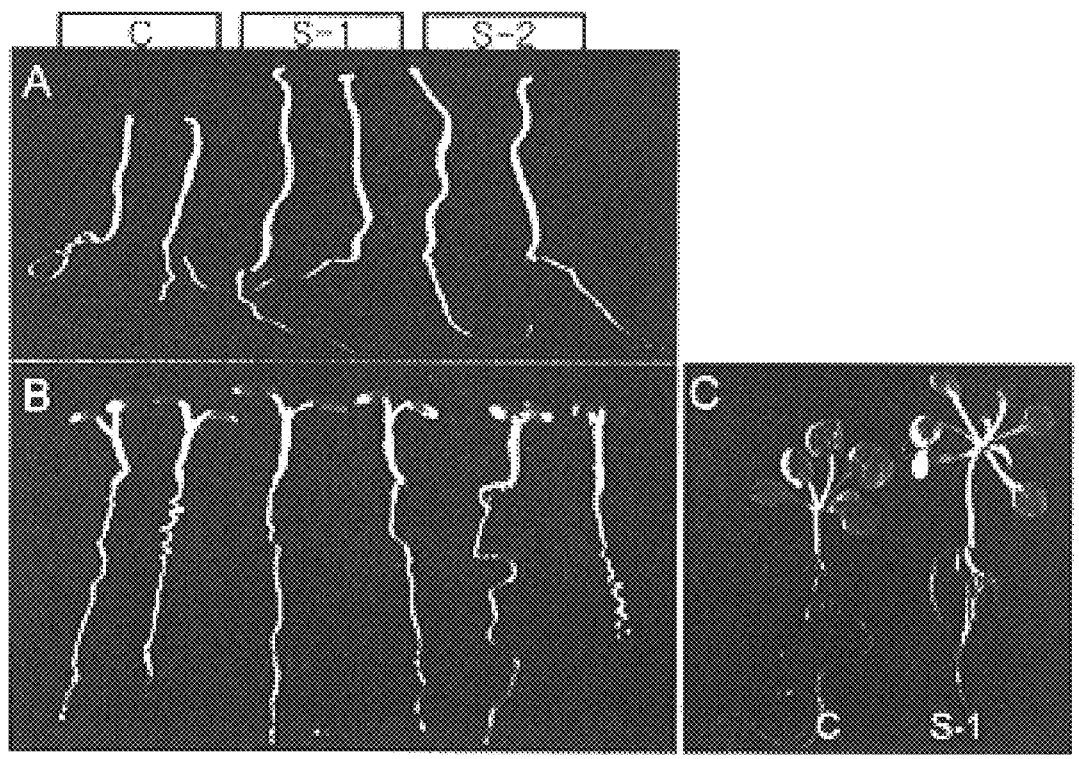
FIG. 6. DDWF1 transgenic Arabidopsis plants. The ddwf1 gene was introduced into Arabidopsis plants in sense orientation. The transgenic plants were grown for 6 days either in complete darkness (A) or in the light (B). Two representative plants of two homozygotic lines (sense-1 and sense-2) are shown. (C) Cells from hypocotyls of the dark-grown transgenic and control plants examined under light microscope.

Our observations indicate that the DDWF1 regulates the BR biosynthesis and that its activity is further induced by the Pra2 in the dark. To get more insights into the regulatory role of the DDWF1 in hypocotyl growth, the ddwf1 gene was introduced into transgenic Arabidopsis plants. The transgenic plants overexpressing the DDWF1 exhibited much longer hypocotyls than those of the control plants both under the light and dark. (FIG. 6). On the contrary other plant parts were not significantly affected. These observations reveal that the DDWF1 is functional only in the hypocotyl growth but not in other plant parts, which is consistent with the expression patterns of the Pra2 and DDWF1 and their organ-specific distributions. It is also clear that the DDWF1 requires a cofactor(s) that is specific to the hypocotyls or stems. Moreover it appears that the DDWF1 is modulated by two regulatory pathways. In the light the DDWF1 is maintained at a basal level, which is still enough for photomorphogenic stem growth (FIGS. 6B and 6C). In the dark the DDWF1 is further up-regulated by the Pra2 (FIG. 6A). Taken together, these indicate that the DDWF1-Pra2 interaction is a molecular mechanism for the dark developmental process of seedlings, particularly the hypocotyl growth, which is a critical mechanism for plants to efficiently reach the light source (Arnim and Deng, 1996). However the Pra2-DDwf1 interaction does not seem to be a significant regulatory factor in the light-grown plants.

Small GTPase-Cytochrome P450 Interaction in Plants

We conclude from our experiments that the DDWF1 is a functional effector of the Pra2 small GTPase and that the Pra2-DDWF1 interaction is a direct molecular clue for the integration of light with BR signals in the dark developmental pathway in plants. Cytochrome P450 enzymes form multi-component complexes with other supplementary proteins on ER membrane for the full activity (Diekmann et al., 1994). The Pra2 could directly activate the DDWF1 enzyme or trigger the formation of functional enzyme complexes on ER membrane. Alternatively, It would bring an essential cofactor(s) via membrane traffic to the DDWF1 enzyme complex. The transgenic Arabidopsis plants that overexpress the DDWF1 exhibit enhanced stem growth even in the light but without any significant phenotypic changes in other plant parts. This characteristic resembles the hypocotyl growth in etiolated seedlings. It is therefore predicted that hypocotyl (or stem)-specific cofactors, either ER membrane-bound or cytosolic or both, are required for the Pra2-DDWF1 interaction. In addition, GTPases are molecular switches that cycle between the GTP-bound active form and the GDP-bound inactive form. The GTP-bound Pra2 is localized to ER membrane where it associates with the DDWF1. Taken together, it is more likely that the Pra2 triggers the formation of the functional DDWF1 enzyme complexes on the ER membrane rather than it directly activates the DDWF1.

Cytochrome P450 enzymes carry out numerous biosynthetic processes in plants (Lester et al., 1997; Rouleau et al., 1999). The Pra2-DDWF1 interaction is the first cytochrome P450-small GTPase interaction reported in plants. However there is a well-characterized precedent in animal systems. The cytochrome $B_{558}$-Rac small GTPase interaction has been extensively studied (Diekmann et al., 1994; Nisimoto et al., 1997; Wittstock and Halkier, 2000). Plasma membrane-bound cytochrome $B_{558}$, upon stimulation by microbial infection, associates with two cytosolic partners, p67$^{phox}$ and p47$^{phox}$, to assemble a multi-component NADPH oxidase complex. Rac small GTPase is also required for the formation of functional enzyme complex through direct interaction with p67$^{phox}$ and also likely with the cytochrome $B_{558}$ (Nisimoto et al., 1997). A similar mechanism would be involved in the Pra2-DDWF1 interaction. In accordance with this assumption, it is notable that small GTPases have been recently implicated to play regulatory roles in the elongation of pollen tube in plants (Kost et al., 1999b; Li et al., 1999), one of the richest sources for endogenous BR hormones in plants. The pollen tube development is also severely affected by BR-deficiency, resulting in male sterility due to retarded growth of pollen tube. Elongating root hairs would be regulated by an essentially identical molecular process (Kost et al., 1999a). This also could be related with our observation that the expression level of the ddwf1 gene in roots is higher in light-grown plants than in dark-grown plants (FIG. 1C), suggesting a role for the DDWF1 on cell elongation in root hairs.

The Pra2 and Pra3 small GTPases have 65% sequence homology through the whole sequences. Both are dark-induced and expressed only in the epicotyls. However, the DDWF1 associates exclusively with the Pra2 not with the Pra3. This suggests that each small GTPase in plants may have a distinct role in various cellular processes in plants. It is also consistent with the fact that the effectors that interact with small GTPases identified so far show extensive structural and functional diversity (Echard et al., 1998; Ueda et al., 2000).

Regulation of Pra2 and DDWF1 Expression: Independent or Interactive?

Figure 7:
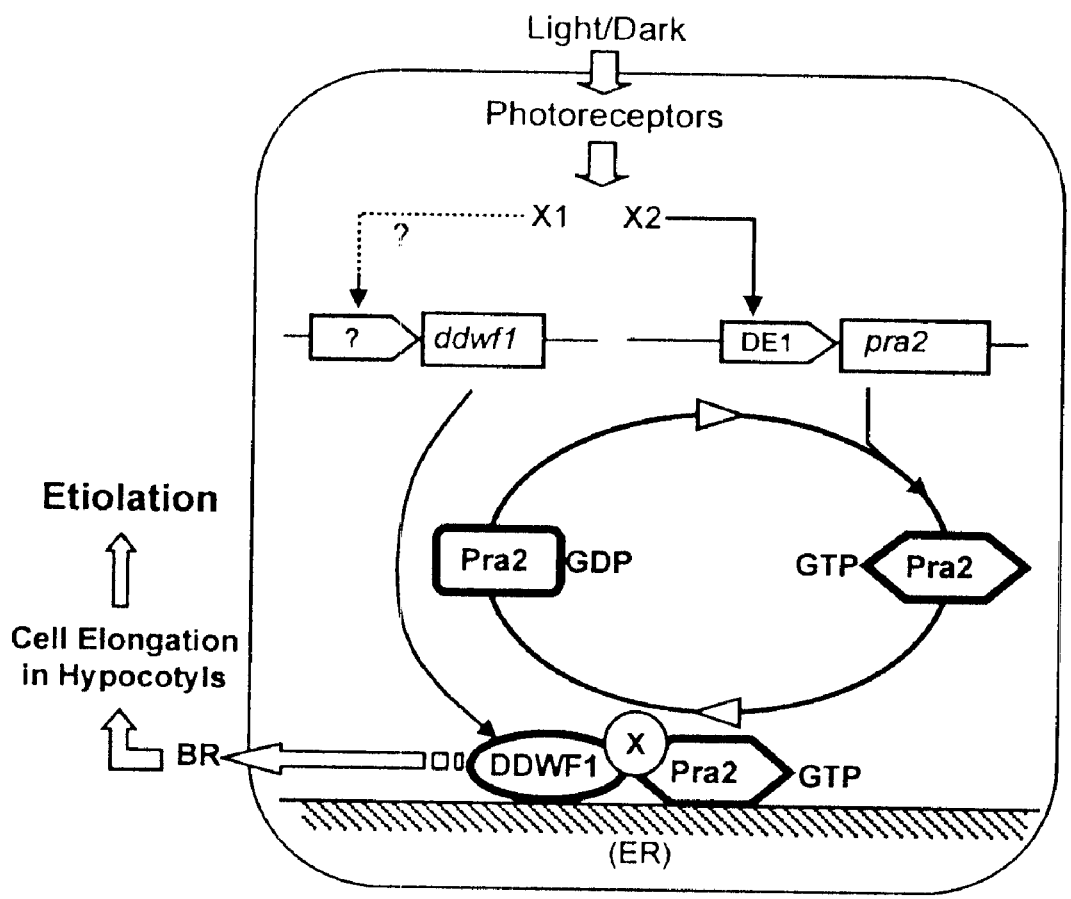
FIG. 7. A working model for the Pra2-DDWF1 interaction. Pra2 GTPase functions as a molecular mediator that integrates light and BR signals in the epicotyl growth of etiolated pea seedlings. The Pra2 would either directly activate the DDWF1 or facilitate the formation of a multi-component cytochrome complex at ER membrane by recruiting other ER-associated or cytoplasmic factors (indicated by X).

Bases on our results, we favor a working model for the Pra2-DDWF1 interaction as depicted in FIG. 7. In the dark, the Pra2 is induced and localized to ER after GTP association. The ER-bound Pra2 activates the DDWF1 either by triggering formation of functional enzyme complexes or by recruiting cytosolic cofactor(s) (factor X in FIG. 7) to the DDWF1. Our observations indicate that the Pra2 localization is regulated by two subsequent steps, one by the dark-induced expression and the other by the GTP association. On the contrary the DDWF1 seems to be destined to associate with ER as it is expressed. These suggest that the Pra2 activity can be also modulated by other factors, such as environmental stress, as well as by light through the GTP-GDP cycle. Taken together our observations strongly suggest that the Pra2 and DDWF1 are regulated by two separate photoregulatory pathways. However, they would not be completely independent but share common steps in the signaling cascade.

Another question is which photoreceptors regulate the Pra2-DDWF1 interaction. The DE1 element of the pra2 gene responds to light signals from phytochromes and blue light photoreceptors (Inaba et al., 1999; Inaba et al., 2000). It is therefore evident that the light itself regardless of wavelengths represses the expression of the Pra2, which is also consistent with the hypothesis that the Pra2 is a molecular switch that modulates the etiolation process in plants. The ddwf1 gene would be regulated in a similar manner as in the pra2 gene. Analyses of the 5' nontranslating region of the ddwf1 gene would elucidate this question. It has been reported that a nuclear factor, although not isolated yet, specifically bound to the DE1 element only in the dark, indicating that it is a positive regulator for the pra2 expression (Inaba et al., 1999). It would be interesting to examine whether this trans-acting factor also binds to the promoter region of the ddwf1 gene.

Role of the Pra2-DDWF1 Interaction in Seedling Development

Seedling development is one of the developmental processes that are most responsive to light condition. Dark-grown seedlings are remarkably different from those grown in the light or under light-dark cycle (Arnim and Deng, 1996). The seedlings in the dark developmental pathway (etiolated) exhibit an accelerated cell elongation in the hypocotyls but with minimal growth in leaf and root to reach the light. On the contrary, those in the light-regulated development (photomorphogenic) build up a morphology optimized for autotrophic photosynthesis (Arnim and Deng, 1996). The etiolation of seedlings is thus to be considered as an active and integrative physiological process that is critical for survival in nature.

We show here that the Pra2-mediated integration of light and BR signals is a molecular basis for the etiolation-deetiolation transition. The Pra2 could be regarded as a positive regulator for the etiolation but a negative regulator for the photomorphogenesis. It is evident that the Pra2 does not regulate the whole BR biosynthetic pathway. The DDWF1 is likely to be expressed to a certain level and functional through the life span even in the light. Our data indicate that the DDWF1 is further induced and activated by the Pra2 in the dark, especially in seedling development. In some plants, the CS, rather than the BL, is considered to be the active BR. It is therefore reasonable that the Pra2 is a photoregulatory molecular switch that regulates the BR biosynthesis through the C-2 hydroxylations, rather than the CS to BL conversion. The light-mediated C-2 hydroxylation would be an universal regulatory mechanism for the dark developmental growth in plants, if not all.

REFERENCES

Arnim, von A., and Deng, X.-W. (1996). Light control of seedling development. Annu. Rev. Plant Physiol. Plant Mol. Biol. 47, 215–243.

Asami, T., and Yoshida, S. (1999). Brassinosteroid biosynthesis inhibitors. Trends Plant Sci. 4, 348–353.

Azpiroz, R., Wu, Y., LoCascio, J. C., and Feldmann, K. A. (1998). An Arabidopsis brassinosteroid-dependent mutant is blocked in cell elongation. Plant Cell 10, 219–230.

Bibikova, T. N., Blancaflor, E. B., and Gilory, S. (1999). Microtubules regulate tip growth and orientation in root hairs of Arabidopsis thaliana. Plant J. 17, 657–665.

Bishop, G. J., Nomura, T., Yokota, T., Harrison, K., Noguchi, T., Fujioka, S., Takatsuto, S., Jones, D. G., and Kamiya, Y. (1999). The tomato DWARF enzyme catalyzes C-6 oxidation in brassinosteroid biosynthesis. Proc. Natl. Acad. Sci. USA 96, 1761–1766.

Bowler, C., Neuhaus, G., Yamagata, H., and Chua, N. H. (1994). Cyclic GMP and calcium mediate phytochrome phototransduction. Cell 77, 73–81.

Briggs, W. R., and Huala, E. (1999). Blue-light photoreceptors in higher plants. Annu. Rev. Cell Dev. Biol. 15, 33–62.

Briggs, W. R., and Siegelman, H. W. (1965). Distribution of phytochrome in etiolated seedlings. Plant Physiol. 40, 934–941.

Choe, S., Dilkes, B. P., Fujioka, S., Takatsuto, S., Sakurai, A., and Feldmann, K. A. (1998). The DWF4 gene of Arabidopsis encodes a cytochrome P450 that mediates a multiple 22α-hydroxylation steps in brassinosteroid biosynthesis. Plant Cell 10, 231–243.

Choe, S., Dilkes, B. P., Gregory, B. D., Ross, A. S., Yuan, H., Noguchi, T., Fujioka, S., Takatsuto, S., Tanaka, A., Yoshida, S., Tax, F. E., and Feldmann, K. A. (1999a). The Arabidopsis dwarf1 mutant is defective in the conversion of 24-methylenecholesterol to campesterol in brassinosteroid biosynthesis. Plant Physiol. 119, 897–907.

Choe, S., Noguchi, T., Fujioka, S., Takatsuto, S,m Tissier, C, P., Gregory, B. D., Ross, A. S., Tanaka, A., Yoshida, S., Tax, F. E., and Feldmann, K. A. (199b). The Arabidopsis dwf7/ste1 is defective in the delta7 sterol C-5 desaturation step leading to brassinosteroid biosynthesis. Plant Cell 11, 207–221.

Chory, J. (2000). Light: an indicator of time and place. Genes. Dev. 14, 257–271.

Clough, S. J., and Bent, A. F. (1998). Floral dip: a simplified method for Agrobacterium-mediated transformation of Arabidopsis thaliana. Plant J. 16, 735–743.

Clouse, S. D., and Sasse, J. M. (1998). Brassinosteroids: Essential regulators of plant growth and development. Annu. Rev. Plant Physiol. Plant Mol. Biol. 49, 427–451.

Cosgrove, D. (1997). Relaxation in a high-stress environment: the molecular basis of extensible cell walls and enlargement. Plant Cell 9, 1031–1041.

Diekmann, D., Abo, A., Johnston, C., Segal, A. W., and Hall, A. (1994). Interaction of Rac with $p67^{phox}$ and regulation of phagocytic NADPH oxidase activity. Science 265, 531–533.

Echard, A., Jollivet, F., Martinez, O., Lacapère, J.-J., Rousselet, A., Janoueix-Lerosey, I., and Goud, B. (1998). Interaction of a Golgi-associated kinesin-like protein with Rab6. Science 279, 580–585.

Exton, J. H. (1998). Small GTPases minireview series. J. Biol. Chem. 273, 19923.

Friedborg, I., Kuusk, S., Moritz, T., and Sundberg, E. (1999). The Arabidopsis Dwarf mutant shi exhibits reduced gibberellin responses conferred by overexpression of a new putative zinc finger protein. Plant Cell 11, 1019–1031.

Fujioka, S., Li, J., Choi, Y. H., Seto, H., Takatsuto, S., Noguchi, T., Watanabe, T., Kuriyama, H., Yokota, T., Chory, J., and Sakurai, A. (1997). The Arabidopsis deetiolated2 mutant is blocked early in brassinosteroid biosynthesis. Plant Cell 9, 1951–1962.

Fujioka, S., Noguchi, T., Watanabe, T., Takatsuto, S., and Yoshida, S. (2000). Biosynthesis of brassinosteroids in cultured cells of Catharanthus roseus. Phytochem. 53, 549–553.

He, Z., Wang, Z.-Y., Li, J., Zhu, Q., Lamb, C., Ronald, P., and Chory, J. (2000). Perception of brassinosteroids by the extracellular domain of the receptor kinase BRI1. Science 288, 2360–2363.

Higashijima, T., Ferguson, K. M., Smigel, M. D., and Gilman, A. G. (1987). The effect of GTP and $Mg^{2+}$ on the GTPase activity and the fluorescent properties of $G_o$. J. Biol. Chem. 262, 757–761.

Horsch, R. B., Fry, J. E., Hoffmann, N. L., Eichholtz, D., Rogers, S. G., and Fraley, R. T. (1985). A simple and general method for transferring genes into plants. Science 227, 1229–1231.

Hooley, R. (1998). Plant hormone perception and action: a role for G-protein signal transduction. Philos. Trans. R. Soc. Lond. B Biol. Sci. 353, 1425–1430.

Inaba, T., Nagano, Y., Sakakibara, T., and Sasaki, Y. (1999). Identification of cis-regulatory element involved in phytochrome down-regulated expression of the pea small GTPase gene pra2. Plant Physiol. 120, 491–499.

Inaba, T., Nagano, Y., Reid, J. M., and Sasaki, Y. (2000). DE1, a 12-base pair cis-regulatory element sufficient to confer dark-inducible and light down-regulated expression to a minimal promoter in pea. J. Biol. Chem. 275, 19723–19727.

Kamiya, Y., and Garcia-Martinez, J. L. (1999). Regulation of gibberellin biosynthesis by light. Curr. Opin. Plant Biol. 2, 398–403.

Kim, B. C., Soh, M. S., Hong, S. H., Furuya, M., and Nam, H. G. (1998). Photomorphogenic development of the Arabidopsis shy2-1D mutation and its interaction with phytochromes in darkness. Plant J. 15, 61–68.

Kost, B., Mathur, J., and Chua, N.-H. (1999a). Cytoskeleton in plant development. Curr. Opin. Plant Biol. 2, 462–470.

Kost, B., Lemichez, E., Spielhofer, P., Hong, Y., Tolias, K., Carpenter, C., and Chua, N.-H. (1999b). Rac homologues and compartmentalized phosphatidylinositol 4,5-biphosphate act in a common pathway to regulate polar pollen tube growth. J. Cell Biol. 145, 317–330.

Lester, D. R., Ross, J. J., Davies, P. J., and Reid, J. B. (1997). Mendel's stem length gene (Le) encodes a gibberellin 3β-hydroxylase. Plant Cell 9, 1435–1443.

Li, J., and Chory, J. (1997). A putative leucine-rich repeat receptor kinase involved in brassinosteroid signal transduction. Cell 90, 929–938.

Li, J, Nagpal, P., Vitart, V., McMorris, T. C., and Chory, J. (1996). A role for brassinosteroids in light-dependent development of Arabidopsis. Science 272, 398–401.

Li, H., Lin, Y., Heath, R. M., Zhu, M. X., and Yang, Z. (1999). Control of pollen tube tip growth by a Rop GTPase-dependent pathway that leads to tip-localized calcium influx. Plant Cell 11, 1731–1742.

Ma, H. (1994). GTP-binding proteins in plants: new members of an old family. Plant Mol. Biol. 26, 1611–1636.

Matzke, M. A., and Matzke, A. J. (1995). Homology-dependent gene silencing in transgenic plants: what does it really tell us? Trends Genet. 11, 1–3.

Mancinelli, A. L. (1994). The physiology of phytochrome action. In Photomorphogenesis in Plants, $2^{nd}$ ed., R. E., Kendrick and G. H. M. Kronenberg, eds. (Dordrecht, The Netherlands: Kluwer Academic Publishers), pp. 211–269.

Nagano, Y., Okada, Y., Narita, H., Asaka, Y., and Sasaki, Y. (1995). Location of light-repressible, small GTP-binding protein of the YPT/rab family in the growing zone of etiolated pea stems. Proc. Natl. Acad. Sci. USA 92, 6314–6318.

Nicol, F., His, I., Jauneau, A., Vernhettes, S., Canut, H., and Höfte, H. (1998). A plasma membrane-bound putative endo-1,4-β-D-glucanase is required for normal wall assembly and cell elongation in Arabidopsis. EMBO J. 17, 5563–5576.

Nisimoto, Y., Freeman, J. L. R., Motalebi, S. A., Hirshberg, M., and Lambeth, J. D. (1997). Rac binding to $p67^{phox}$. J. Biol. Chem. 272, 18834–18841.

Noguchi, T., Fujioka, S., Choe, S., Takatsuto, S., Yoshida, S., Yuan, H., Feldmann, K. A., and Tax, F. E. (1999). Brassinosteroid-insensitive dwarf mutants of Arabidopsis accumulate brassinosteroids. Plant Physiol. 121, 743–752.

Nomura, T., Kitasaka, Y., Takatsuto, S., Reid, J. B., Fukami, M., and Yokota, T. (1999). Brassinosteroid/sterol synthesis and plant growth as affected by lka and lkb mutations of pea. Plant Physiol. 119, 1517–1526.

Pompon, D., Lourat, B., Bronine, A., and Urban, P. (1996). Yeast expression of animal and plant P450s in optimized redox environment. Methods Enzymol. 272, 51–64.

Quail, P. H. (1997). The phytochromes: a biochemical mechanism of signaling in sight? BioEssays 19, 571–579.

Romero, L. C., Sommer, D., Gotor, C., and Song, P. S. (1991). G-proteins in etiolated Avena seedlings possible phytochrome regulation. FEBS Lett. 282, 341–346.

Rouleau, M., Marsolais, F., Richard, M., Nicolle, L., Voigt, B., Adam, G., and Varin, L. (1999). Inactivation of Brassinosteroid biological activity by a salicylate-inducible steroid sulfotransferase from Brassica napus. J. Biol. Chem. 274, 20925–20930.

Roux, S. J. (1994). Signal transduction in phytochrome responses. In Photomorphogenesis in Plants. $2^{nd}$ ed., R. E., Kendrick and G. H. M. Kronenberg, eds. (Dordrecht, The Netherlands: Kluwer Academic Publishers), pp. 187–209.

Sakurai, A., and Fujioka, S. (1997). Studies on biosynthesis of brassinosteroids. Biosci. Biotechnol. Biochem. 61, 757–762.

Salchert, K., Bhalerao, R., Koncz-Kálmán, Z., and Koncz, C. (1998). Control of cell elongation and stress responses by steroid hormones and carbon catabolic repression in plants. Phil. Trans. R. Soc. Lond. B 353, 1517–1520.

Sambrook, J., Fritsch, E. F., and Maniatis, T., eds. (1989). Molecular cloning: a laboratory manual (New York: Cold Spring Harbor Laboratory Press).

Schumacher, K., and Chory, J. (2000). Brassinosteroid signal transduction: still casting the actors. Curr. Opin. Plant Biol. 3, 79–84.

Scita, G., Tenca, P., Frittoli, E., Tocchetti, A., Innocenti, M., Giardina, G., and Di Fiore, P. P. (2000). Signaling from Ras to Rac and beyond: not just a matter of GEFs. EMBO J. 19, 2393–2398.

Senger,. H., and Schmidt, W. (1994). Diversity of photoreceptors. In Photomorphogenesis in Plants, $2^{nd}$ ed., R. E., Kendrick and G. H. M. Kronenberg, eds. (Dordrecht, The Netherlands: Kluwer Academic Publishers), pp. 301–325.

Sommer, D., and Song, P.-S. (1994). Isolation and purification of a small-molecular-weight GTP-binding protein from plants. Protein Expr. Purif. 5, 402–408.

Szekeres, M., Németh, K., Koncz-Kálmán, Z., Mathur, J., Kauschmann, A., Altmann, T., Rédei, G. P., Nagy, F., Schell, J., and Koncz, C. (1996). Brassinosteroids rescue the deficiency of CYP90, a cytochrome P450, controlling cell elongation and deetiolation in Arabidopsis. Cell 85, 171–182.

Ueda, T., Matsuda, N., Uchimiya, H., and Nakano, A. (2000). Modes of interaction between the Arabidopsis Rab protein, Ara4, and its putative regulator molecules revealed by a yeast expression system. Plant J. 21, 341–349.

Waxman, D. J. (1991). P450-catalyzed steroid hydroxylation: Assay and product identification by thin-layer chromatography. Methods Enzymol. 206, 462–476.

Wittstock, U., and Halkier, B. A. (2000). Cytochrome P450 CYP79A2 from Arabidopsis thaliana L. catalyzes the conversion of L-phenylalanine to phenylacetaldoxime in the biosynthesis of benzylglucosinolate. J. Biol. Chem. 275, 14659–14666.

Xu, W., Purugganan, M. M., Polisensky, D. H., Antosiewicz, D. M., Fry, S. C., and Braam J. (1995). Arabidopsis TCH4, regulated by hormones and the environment, encodes a xyloglucan endotransglycosylase. Plant Cell 7, 1555–1567.

Yoshida, K., Nagano, Y., Murai, N., and Sasaki, Y. (1993). Phytochrome-regulated expression of the genes encoding the small GTP-binding proteins in peas. Proc. Natl. Acad. Sci. USA 90, 6636–6640.

What is claimed is:

1. A transformed host cell which is stably transformed with a vector containing the nucleic acid molecule given in SEQ ID NO: 1 ligated to at least one regulatory element for the expression of the cytochrome P450 hydroxylase in prokaryotic or eukaryotic cells.

2. The transformed host cell according to claim 1, wherein the host cell is a prokaryotic, fungal, plant or animal cell.

3. The transformed E. coli XL1-Blue DDWF1 having the Accession No. KCTC 0857BP.

4. The transformed host cell according to claim 1, wherein said at least one regulatory element are selected from the group consisting of promoters, terminators and signals for polyadenylation.

5. As isolated nucleic acid molecule encoding a cytochrome P450 hydroxylase or a fragment thereof that catalyzes the conversion from typhasterol to castasterone, said hydroxylase having the amino acid sequence given in SEQ ID NO: 2.

6. An isolated nucleic acid molecule comprising: (1) a nucleic acid sequence encoding a cytochrome P450 hydroxylase, said nucleic acid sequence comprising the coding region of the nucleotide sequence given in SEQ ID NO: 1, or (2) a fragment of said nucleic acid sequence that catalyzes the conversion from typhasterol to castasterone.

* * * * *

SEQUENCE LISTING

<160> NUMBER OF SEQ ID NOS: 4

<210> SEQ ID NO 1
<211> LENGTH: 1488
<212> TYPE: DNA
<213> ORGANISM: Pisum sativum

<400> SEQUENCE: 1

```
atggcactac aagtattgac acttcctagt tgggtcacat tgttcaccac atttgccatc      60
ctcctcctct tcagccgccg tctccgccgc cgccaatata atctcccacc aggcccaaaa     120
ccatggccca taataggaaa cttcaacctt attggaaccc tcccacacca atccctccat     180
gggctcaccc aaaaatatgg acctattatg catctatggt tcggctccaa acgcgtcgtc     240
gtgggctcaa ctgtagaaat ggcgaaagcc tttctcaaaa cccacgacgc aacgttagcc     300
ggccgaccca aattctctgc cggaaaatac acaacttata actactctga cataacttgg     360
tctcagtacg tccgtattg gcgccaagct cggagaatgt gtctattaga attgtttagt     420
gcaaaacgtc ttgagtctta tgagtacata agaaaacaag agttacatgt ttttttacat     480
gaactctttg attctagaaa caaaacaatt ttgttgaaag accatctttc aagtttgagt     540
ctaaatgtta taagtagaat ggtgttagga aggaaatatc tagagaaggt tgaaaattct     600
attatttctc cggatgagtt taagaatatg ttggatgagt tgttttttgct taatgggatt     660
cttaatattg gggattttat tccttggatt catttcttag attttcaagg gtatgtgaag     720
aggatgaagg ttttgagtaa aaagtttgat ggatttatgg aacatgtgtt ggaggaacat     780
attgaaagaa gaaaaggtgt taaggattat gttgctaagg atatggtgga tgttctttg     840
caacttgctg aggatcctga tcttgaagtc aaacttgaaa gacatggtgt taaagctttt     900
actcaggact tgatagcagg agggacagag agctcagcag tgacagtaga atgggcaatc     960
tcagagctaa taagaaaacc agaaatcttc aagaaagcaa cagaggaact agacagagta    1020
ataggaagag aaagatgggt tgaagagaaa gacattgcta atctacctta tgtttatgca    1080
attgctaaag aaacaatgag acttcaccca gtggcaccaa tgttagtacc aagagaagct    1140
agagaagatt gcaatatcaa tggatatgat attccaaaag ggtcttttgat tcttgttaat    1200
acttggacaa ttgcaagaga ttctaatgtt tgggataatc caaatgagtt tatgccagag    1260
aggtttcttg gtaaggatat agatgtgaaa ggacatgatt atgagttgtt gccatttggt    1320
gctggtagaa gaatgtgtcc tggttaccct cttggtatta aggttattca atcaagtttg    1380
gctaatttgt tgcatggatt taattggaga ttgagtgatg atgtgaaaaa agaggatttg    1440
aatatggagg agattttttgg gctttctaca cctaagaaga tccattag                1488
```

<210> SEQ ID NO 2
<211> LENGTH: 495
<212> TYPE: PRT
<213> ORGANISM: Pisum sativum

<400> SEQUENCE: 2

```
Met Ala Leu Gln Val Leu Thr Leu Pro Ser Trp Val Thr Leu Phe Thr
1               5                   10                  15
```

-continued

```
Thr Phe Ala Ile Leu Leu Phe Ser Arg Arg Leu Arg Arg Gln
         20              25              30

Tyr Asn Leu Pro Pro Gly Pro Lys Pro Trp Pro Ile Ile Gly Asn Phe
             35              40              45

Asn Leu Ile Gly Thr Leu Pro His Gln Ser Leu His Gly Leu Thr Gln
 50              55              60

Lys Tyr Gly Pro Ile Met His Leu Trp Phe Gly Ser Lys Arg Val Val
 65              70              75              80

Val Gly Ser Thr Val Glu Met Ala Lys Ala Phe Leu Lys Thr His Asp
             85              90              95

Ala Thr Leu Ala Gly Arg Pro Lys Phe Ser Ala Gly Lys Tyr Thr Thr
             100             105             110

Tyr Asn Tyr Ser Asp Ile Thr Trp Ser Gln Tyr Gly Pro Tyr Trp Arg
             115             120             125

Gln Ala Arg Arg Met Cys Leu Leu Glu Leu Phe Ser Ala Lys Arg Leu
             130             135             140

Glu Ser Tyr Glu Tyr Ile Arg Lys Gln Glu Leu His Val Phe Leu His
145             150             155             160

Glu Leu Phe Asp Ser Arg Asn Lys Thr Ile Leu Leu Lys Asp His Leu
                 165             170             175

Ser Ser Leu Ser Leu Asn Val Ile Ser Arg Met Val Leu Gly Arg Lys
                 180             185             190

Tyr Leu Glu Lys Val Glu Asn Ser Ile Ile Ser Pro Asp Glu Phe Lys
             195             200             205

Asn Met Leu Asp Glu Leu Phe Leu Leu Asn Gly Ile Leu Asn Ile Gly
 210             215             220

Asp Phe Ile Pro Trp Ile His Phe Leu Asp Phe Gln Gly Tyr Val Lys
225             230             235             240

Arg Met Lys Val Leu Ser Lys Lys Phe Asp Gly Phe Met Glu His Val
                 245             250             255

Leu Glu Glu His Ile Glu Arg Arg Lys Gly Val Lys Asp Tyr Val Ala
             260             265             270

Lys Asp Met Val Asp Val Leu Leu Gln Leu Ala Glu Asp Pro Asp Leu
 275             280             285

Glu Val Lys Leu Glu Arg His Gly Val Lys Ala Phe Thr Gln Asp Leu
 290             295             300

Ile Ala Gly Gly Thr Glu Ser Ser Ala Val Thr Val Glu Trp Ala Ile
305             310             315             320

Ser Glu Leu Ile Arg Lys Pro Glu Ile Phe Lys Lys Ala Thr Glu Glu
                 325             330             335

Leu Asp Arg Val Ile Gly Arg Glu Arg Trp Val Glu Glu Lys Asp Ile
             340             345             350

Ala Asn Leu Pro Tyr Val Tyr Ala Ile Ala Lys Glu Thr Met Arg Leu
             355             360             365

His Pro Val Ala Pro Met Leu Val Pro Arg Glu Ala Arg Glu Asp Cys
             370             375             380

Asn Ile Asn Gly Tyr Asp Ile Pro Lys Gly Ser Leu Ile Leu Val Asn
385             390             395             400

Thr Trp Thr Ile Ala Arg Asp Ser Asn Val Trp Asp Asn Pro Asn Glu
                 405             410             415

Phe Met Pro Glu Arg Phe Leu Gly Lys Asp Ile Asp Val Lys Gly His
             420             425             430
```

```
Asp Tyr Glu Leu Leu Pro Phe Gly Ala Gly Arg Arg Met Cys Pro Gly
        435                 440                 445

Tyr Pro Leu Gly Ile Lys Val Ile Gln Ser Ser Leu Ala Asn Leu Leu
    450                 455                 460

His Gly Phe Asn Trp Arg Leu Ser Asp Asp Val Lys Lys Glu Asp Leu
465                 470                 475                 480

Asn Met Glu Glu Ile Phe Gly Leu Ser Thr Pro Lys Lys Ile His
                485                 490                 495

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
atggcactac aagtattgac a                                       21

<210> SEQ ID NO 4
<211> LENGTH: 23
<212> TYPE: DNA
<213> ORGANISM: Artificial Sequence
<220> FEATURE:
<223> OTHER INFORMATION: PCR primer

<400> SEQUENCE: 4
ctaatggatc ttcttaggtg tag                                     23
```